United States Patent
Wang

(10) Patent No.: US 6,218,541 B1
(45) Date of Patent: Apr. 17, 2001

(54) METHOD FOR EXTRACTING BISBENZYLISOQUINOLINES

(75) Inventor: Zhishuang Wang, Lexington, KY (US)

(73) Assignee: CBA, International, Inc., Lexington, KY (US)

( * ) Notice: Subject to any disclaimer, the term of this patent is extended or adjusted under 35 U.S.C. 154(b) by 0 days.

(21) Appl. No.: 09/340,830

(22) Filed: Jun. 28, 1999

(51) Int. Cl.[7] .................................................. C07D 221/22
(52) U.S. Cl. ...................................................... 546/35
(58) Field of Search ........................................ 546/140, 35

(56) References Cited

PUBLICATIONS

Chong–hou, Xiao, Chinese Medication Chemistry, Trial edition textbook of medical collge and pharmacy college, p. 106, 1987.*

The Merck Index, Eleventh Edition, Centennial Edition, Merck & Co., Inc, Rahway, N.J. U.S.A., (1989); p. 1455.

* cited by examiner

Primary Examiner—John Kight
Assistant Examiner—Binta Robinson

(74) Attorney, Agent, or Firm—Price, Heneveld, Cooper, DeWitt & Litton

(57) ABSTRACT

A method for obtaining purified bisbenzylisoquinoline alkaloids from the roots of Stephania Tetrandra involves obtaining, from the roots of Stephania Tetrandra, a precipitate comprising tetrandrine, fangchinoline and compounds which constitute impurities, contacting the precipitate with chloroform to form a chloroform solution in which tetrandrine and fangchinoline is dissolved, separating the chloroform solution containing dissolved tetrandrine and fangchinoline from undissolved impurities, removing chloroform from the chloroform solution to obtain a chloroform extract solid having an enriched tetrandrine and fangchinoline content relative to the precipitate, contacting the chloroform extract solid with cool benzene to form a combination comprising undissolved fangchinoline and a benzene solution in which tetrandrine is dissolved, separating the benzene solution from the undissolved fangchinoline from the first solid, removing benzene from the first benzene solution to form a benzene extract which comprises tetrandrine, and subjecting the benzene extract which comprises tetrandrine and subjecting the undissolved fangchinoline to further operations to obtain purified tetrandrine and fangchinoline, separately. The method has the advantages of being able to achieve higher yields of tetrandrine as well as fangchinoline while using lower amounts of benzene, and does not require the use of chromatographic separation columns.

46 Claims, 3 Drawing Sheets

METHOD FOR EXTRACTING BISBENZYLISOQUINOLINES

FIELD OF THE INVENTION

This invention relates to the extraction of bisbenzylisoquinolines from the root of Stephania Tetrandra S. Moore, and more particularly to a method for obtaining purified bisbenzylisoquinolines from the roots of Stephania Tetrandra S. Moore.

The inventor knows of two prior methods for obtaining purified tetrandrine from the roots of Stephania Tetrandra. The first method involves a refluxing operation in which tetrandrine, fangchinoline, cyclanoline, and various impurities are extracted from the roots of Stephania Tetrandra with ethanol. Tetrandrine and fangchinoline, along with various impurities, are then dissolved by acid solution. Hydrophobic impurities are then removed by filtering. Tetrandrine and fangchinoline are dissociated from the basic solution, to form a milky or cloudy suspension, and then are extracted with chloroform. The chloroform is removed, such as by evaporation, and retrieved, and tetrandrine is separated from fangchinoline by passing the resulting residue through an alumina chromatographic column. This first method is extremely slow and relies on the use of relatively expensive chromatographic separation equipment, and therefore is not conducive to commercial production of tetrandrine.

A second known process involves macerating ground roots of Stephania Tetrandra in the presence of an acidic solution to extract tetrandrine, cyclanoline, fangchinoline, and various soluble impurities from the roots of Stephania Tetrandra. The acidic solution (containing tetrandrine, cyclanoline, fangchinoline and various impurities) is then separated from the depleted roots of Stephania Tetrandra. A base is added to the acid solution to cause precipitation of tetrandrine, fangchinoline and various impurities. The basic solution containing cyclanoline is then separated from the precipitate. The precipitate is then contacted with cool benzene to dissolve tetrandrine. The cool benzene solution (containing tetrandrine and a small portion of the fangchinoline) is separated from a solid residue (which contains a substantial portion of the fangchinoline). Next, the benzene solution (containing tetrandrine) is concentrated to remove benzene, and the removed benzene is retrieved. The benzene extract is then dissolved into acetone. A substantial portion of the acetone is removed from the tetrandrine-rich acetone solution, such as by retrieve. The concentrated acetone solution (which is rich in tetrandrine) is then cooled to cause crystallization of tetrandrine along with a small quantity of impurities. The crystallized material is separated from the acetone, such as by filtration. The crystallized material (including tetrandrine) is redissolved in benzene. The benzene solution is then contacted with activated charcoal to adsorb any remaining impurities and to decolor. Thereafter the benzene solution is separated from the activated charcoal (on which any remaining impurities have been adsorbed) and benzene undissolvable fangchinoline, such as by filtration. Benzene is removed from the resulting filtrate, such as by evaporation, and retrieved. The resulting solid residue is combined with alcohol to recrystallize and decolor the tetrandrine. The pure tetrandrine crystals are separated from the alcohol, such as by filtration. A disadvantage with this second known method is that it involves the use of very large quantities of benzene, a hazardous chemical. Further, this second known method yields only about 3 kilograms of tetrandrine for every metric ton of raw material.

Accordingly, neither of the known processes for obtaining purified tetrandrine from the root of Stephania Tetrandra are commercially attractive.

SUMMARY OF THE INVENTION

In the present invention, higher yields of tetrandrine are economically achieved, while concomitantly reducing the amount of hazardous benzene which is required for obtaining purified tetrandrine from the roots of Stephania Tetrandra, and while eliminating the use of a slow and expensive chromatographic separation.

These goals are achieved in the present invention by obtaining an extract from the roots of Stephania Tetrandra with chloroform, separating the chloroform to obtain a first solid, extracting the first solid with benzene and then removing the benzene to yield a second solid comprising tetrandrine.

In another aspect of the invention, fangchinoline is also extracted from the same raw material by purification and recrystalization of the benzene filtrate left after benzene extraction.

These and other objects, advantages and features of the invention will be more fully understood and appreciated by reference to the written specification and appended drawings.

DETAILED DESCRIPTION OF THE PRIOR ART

Figure 1:
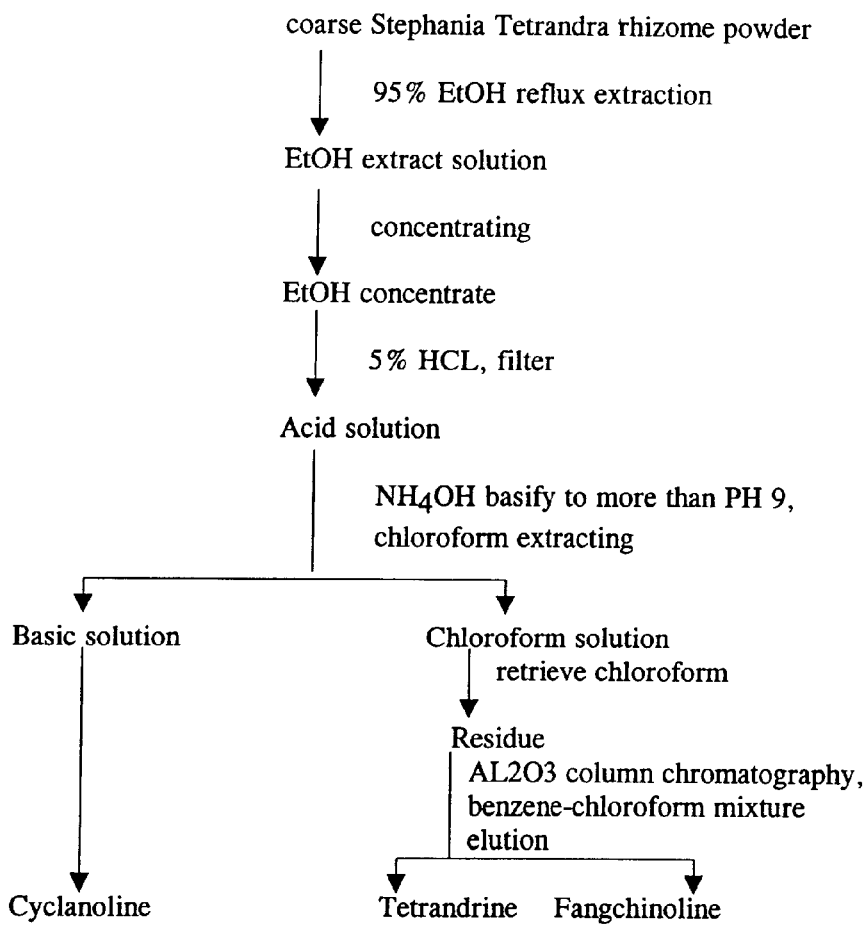
FIG. 1 is a flow diagram for a first known process for recovering tetrandrine from the roots of Stephania Tetrandra.

FIG. 1 illustrates a first known method for obtaining purified tetrandrine and fangchinoline from the roots of Stephania Tetrandra. This method is disclosed by Xiao Chong-Hou et al.; Chinese Medication Chemistry (For Chinese Medication Specialty), Trial Edition Textbook of Medical College and Pharmacy College, Page 106, Shanghai Science and Technique Press, 1987. The first step of the process involves extracting tetrandrine, fangchinoline, and cyclanoline, along with undesirable impurities, from the roots of Stephania Tetrandra in a refluxing operation using ethyl alcohol as solvent. The roots of Stephania Tetrandra are provided in a coarse powdered form, and combined with a 95% ethyl alcohol solution. Tetrandrine, fangchinoline and cyclanoline, as well as certain undesirable impurities, are transferred from the powdered roots to the ethyl alcohol solution. After a desired portion of tetrandrine and other compounds have been extracted from the powdered roots, the ethyl alcohol extract solution in which tetrandrine and other compounds extracted from the roots have been dissolved is separated from the powdered roots, such as by sedimentation and decantation or filtration. The concentrate of tetrandrine and other compounds extracted from the roots of Stephania Tetrandra are produced by removing ethyl alcohol, such as by evaporation. To the ethanol concentrate, 5% hydrochloric acid is added to dissolve tetrandrine and other compounds. The acidified solution is filtered, and hydrophobic impurities are removed by filtration. Filtration acidified solution is then basified with ammonium hydroxide to a pH of at least 9. This causes tetrandrine and fangchinoline to be dissociated from the basic solution, to form a milky or cloudy suspension therein. However, cyclanoline remains in the basic solution. Thus, cyclanoline is separated from tetrandrine and fangchinoline by extracting the suspended tetrandrine and fangchinoline with chloroform under basic solution conditions. Tetrandrine and fangchinoline, and a relatively small portion of undesirable impurities are transferred in chloroform. The chloroform is then separated from the basic solution, and then removed, such as by evaporation, and retrieved, and a solid residue containing tetrandrine and fangchinoline is recovered. In accordance with the prior art method, the residue is dissolved in a solvent comprising a mixture of benzene and chloroform. The solution comprising the dissolved residue and the solvent is passed through an alumina chromatographic column. Tetrandrine and fangchinoline elute from the column at different times, and complete separation of the tetrandrine from the fangchinoline can be achieved. However, as previously noted, this process is extremely slow and requires the use of relatively expensive chromatographic separation apparatuses.

Figure 2:
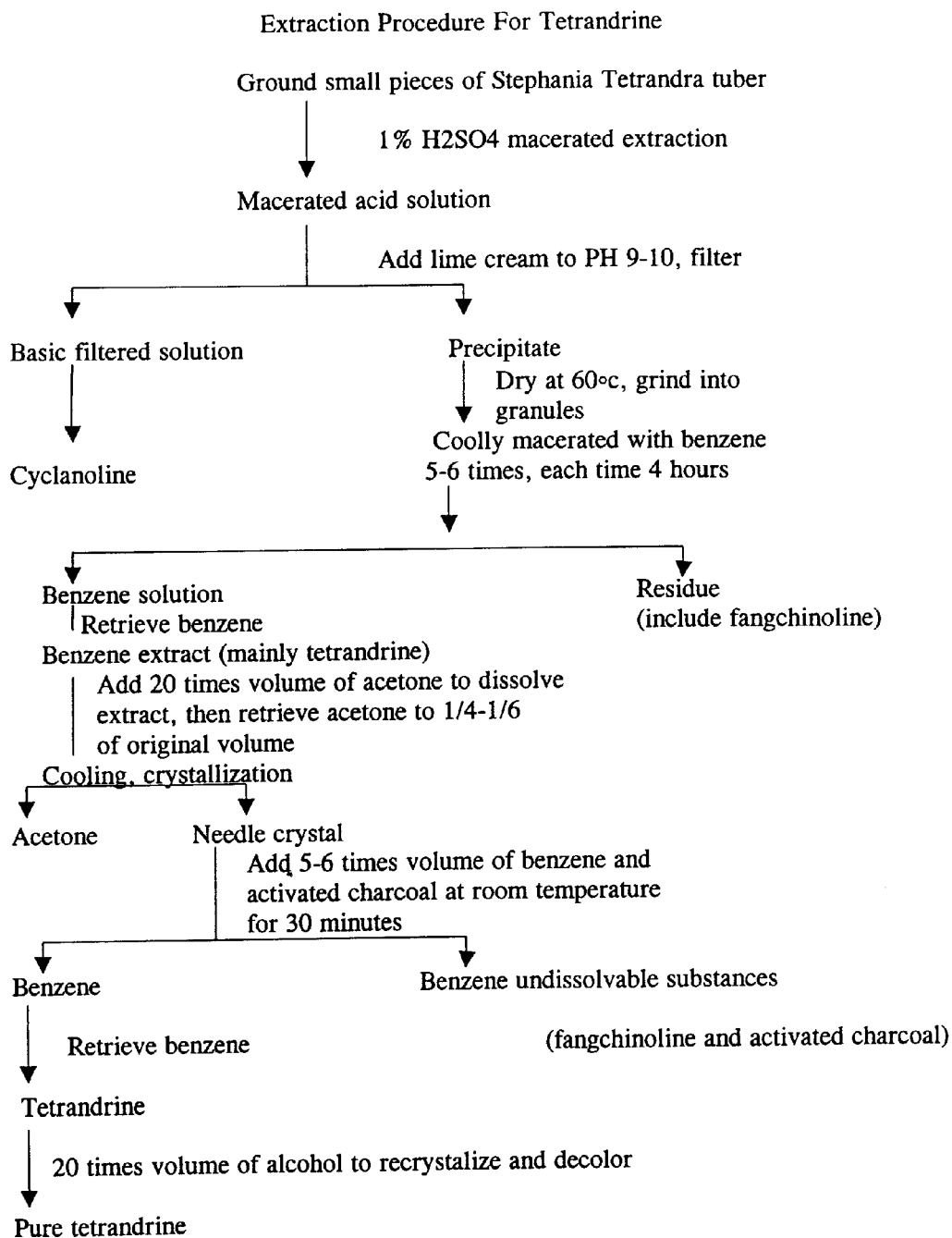
FIG. 2 is a flow diagram for a second known process for extracting tetrandrine from the roots of Stephania Tetrandra.

A second known procedure is illustrated schematically in FIG. 2. This method is described in Beijing Medical College, Beijing Chinese Traditional Medical College; Ingredient Chemistry of Chinese Herbs (For Pharmacy, Chinese Herbs Specialty), Trial Edition Textbook of Medical College and Pharmacy College, Page 132, People's Health Press, 1980. This second method for obtaining purified tetrandrine from materials extracted from the roots of Stephania Tetrandra involves first macerating ground pieces of the roots of Stephania Tetrandra with a dilute acid solution (1% $H_2SO_4$). Tetrandrine, fangchinoline, cyclanoline and undesirable impurities are leached from the ground roots of Stephania Tetrandra by the acid solution. After a sufficient proportion of the tetrandrine and other compounds have been leached from the roots, the roots are separated from the acid solution, such as by expression, sedimentation and decantation, filtration, or a combination thereof. The depleted solids from .which tetrandrine and other compounds have been extracted may be contacted with fresh acid solution to extract additional tetrandrine and other compounds from the roots which were not extracted in the first leaching operation. This step may be repeated as desired until the quantity of tetrandrine and fangchinoline being recovered does not justify further leaching operations. The acid solution(s) obtained from the leaching operation(s) is (are) basified to a pH of from about 9 to about 10, such as with lime cream (calcium hydroxide). Basification of the solution causes tetrandrine, fangchinoline, and various impurities to precipitate. As with the previously described method, cyclanoline remains in the solution and is therefore easily separated from tetrandrine and fangchinoline, such as by sedimentation and decantation or filtration. The precipitate is dried (e.g., at about 60° C.) and ground into granules. The ground precipitate is macerated with cool benzene (e.g., lower than normal room temperature). At lower temperatures, (e.g., temperatures below normal room temperature) tetrandrine is soluble in benzene, while fangchinoline is hard to dissolve. Accordingly, tetrandrine can be separated from fangchinoline by separating undissolved solids from the cool benzene solution, such as by filtration. In this separation, the tetrandrine remains in the cool benzene solution and fangchinoline remains as an undissolved solid. The prior art does not disclose any further processing of the undissolved solids (or residue) separated from the cool benzene solution. This residue, which contains fangchinoline (a valuable therapeutic agent), apparently is not recovered in accordance with the second known process. The benzene is removed from the benzene solution, such as by evaporation, and retrieved, to obtain a residue comprising tetrandrine. The residue recovered from the benzene solution is dissolved in acetone, and tetrandrine is crystallized from the acetone solution. This is achieved by removing some of the acetone from the solution, such as by evaporation, (the evaporated acetone is retrieved) and cooling the solution. Some remaining impurities are removed by separating the liquid acetone from the crystals. A further separation and purification of tetrandrine is achieved by dissolving the crystals recovered from the acetone solution in benzene (at about room temperature) and adding activated charcoal to the benzene solution. The activated charcoal decolors and adsorbs additional impurities. The remaining fangchinoline and activated charcoal on which impurities have been adsorbed are separated from the benzene solution, which contains dissolved tetrandrine and very small quantities of impurities. The tetrandrine and relatively minor amounts of impurities are recovered from the benzene solution by removing the benzene, such as by evaporation (the evaporated benzene is retrieved). The recovered residue (containing mostly tetrandrine) is subjected to a final purification step in which the residue is dissolved in an alcohol (e.g. ethyl alcohol) and subsequently recrystallized. Most of the remaining impurities present in the residue recovered from the benzene solution remain in the alcohol solution during and after recrystallization of the tetrandrine. The recrystallized tetrandrine can be separated from the alcohol solution, and hence separated from the remaining impurities, by filtration. The crystals recovered from the alcohol solution are substantially pure tetrandrine. A disadvantage with this second method of recovering tetrandrine from the roots of Stephania Tetrandra is that it requires the use of very large quantities of benzene, a hazardous chemical. Another disadvantage with this second known method is that only about 3 kilograms of tetrandrine are recovered for every metric ton of Stephania Tetrandra roots, and fangchinoline is not recovered.

DESCRIPTION OF THE PREFERRED EMBODIMENTS

PREFERRED EMBODIMENT GENERAL DISCUSSION

Figure 3:
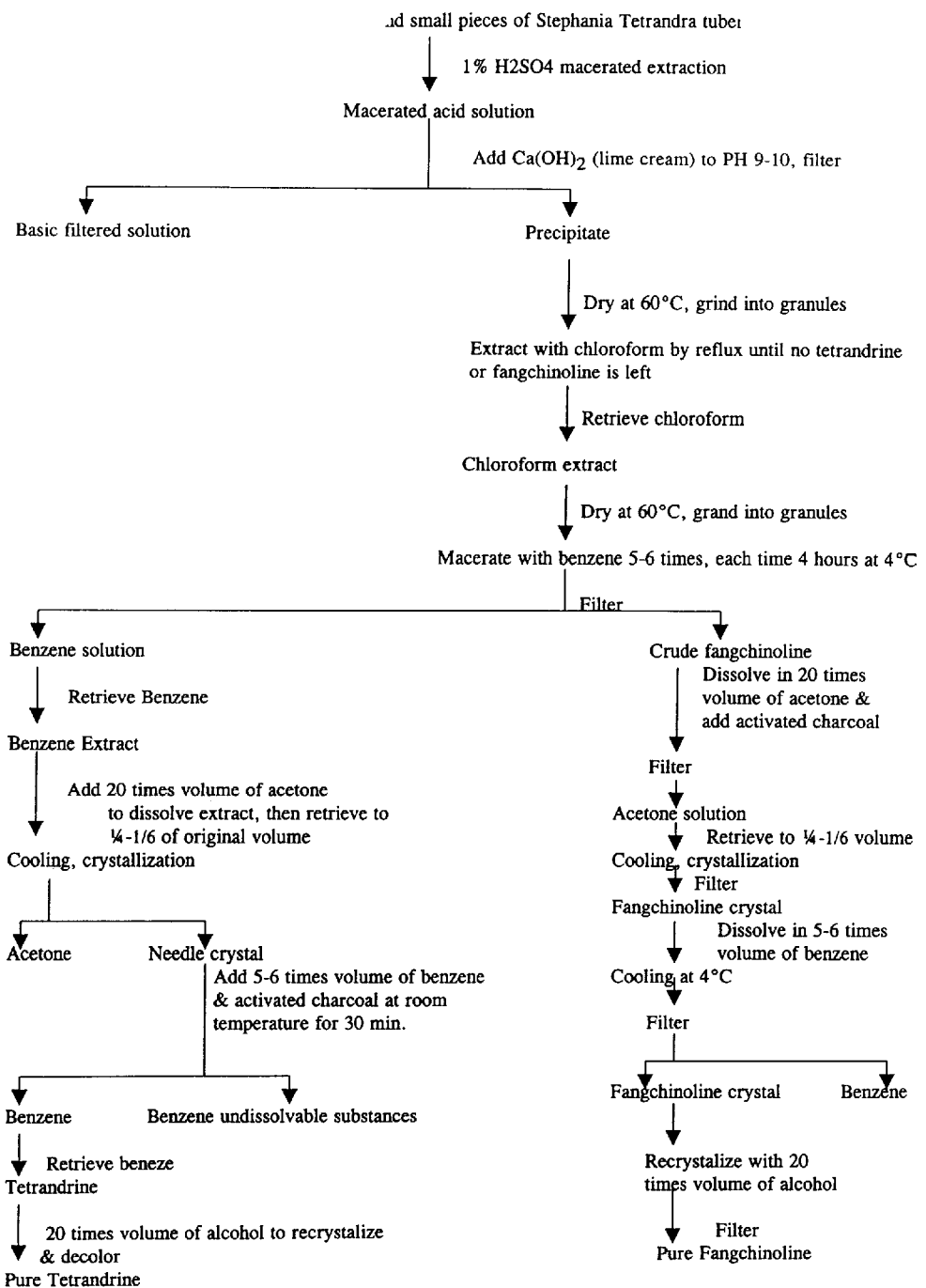
FIG. 3 is a flow diagram showing the process of the preferred embodiments.

A method in accordance with the present invention, for obtaining purified tetrandrine and purified fangchinoline from the roots of Stephania Tetrandra is schematically illustrated in FIG. 3. The method of this invention involves obtaining, from roots of Stephania Tetrandra, a precipitate comprising tetrandrine, fangchinoline and compounds which constitute impurities. This precipitate can be obtained by macerating the roots of Stephania Tetrandra in an acidic solution to leach tetrandrine and fangchinoline from the roots, separating the acidic solution (containing tetrandrine and fangchinoline) from the macerated roots, and adding a base to the acidic solution to form a basic solution and to cause precipitation of tetrandrine and fangchinoline. The resulting precipitate can be separated from the basic solution, such as by decantation, filtration, and dried, such as by evaporation at 60° C. The precipitate is then contacted with chloroform to form a chloroform solution in which tetrandrine and fangchinoline are dissolved. Other compounds present in the precipitate, including impurities which are to be removed and which are insoluble in chloroform, remain undissolved. The chloroform solution containing dissolved tetrandrine and fangchinoline is then separated from the undissolved impurities. A solid having an enriched tetrandrine and fangchinoline content relative to the original precipitate is obtained by removing the chloroform from the chloroform solution, such as by evaporation into a condenser for retrieved. The resulting solid, chloroform extract, having enriched tetrandrine and fangchinoline content is contacted with benzene at 4° C. to form a combination comprising undissolved fangchinoline and a benzene solution in which tetrandrine is dissolved. The undissolved fangchinoline is then separated from the benzene solution, such as by filtration, and the benzene is removed from the benzene solution to form a benzene extract which comprises tetrandrine. This resulting benzene extract is subjected to further operations to obtain purified tetrandrine.

The inventor has discovered that by contacting materials extracted from the roots of Stephania Tetrandra with chloroform it is possible to dissolve substantially all of the tetrandrine and fangclinoline, while leaving substantial amounts of impurities undissolved, thereby facilitating separation of tetrandrine and fangchinoline from a substantial quantity of impurities which are insoluble in chloroform. This separation, involving the use of chloroform, allows tetrandrine and fangchinoline extracted from the roots of Stephania Tetrandra to be purified in a more efficient manner, which provides higher yields of tetrandrine and fangchinoline. The separation step (involving the use of contacting materials leached from the roots of Stephania Tetrandra with chloroform) eliminates the need for chromatographic separation, as required by one of the known methods for extracting and purifying bisbenzylisoquinolines, and requires substantially reduced amounts of benzene as compared with the other known method for extracting and isolating bisbenzylisoquinolines.

In another aspect of the invention, fangchinoline is also extracted and isolated from the same raw material. This is accomplished by separating fangchinoline from the chloroform extract extracted from basic precipitate of the roots of Stephania Tetrandra. The chloroform extract having enriched tetrandrine and fangchinoline content is contacted with benzene at 4° C. in which tetrandrine is soluble and in which fangchinoline is hard to dissolve. The undissolved fangchinoline is separated from benzene, such as by filtration, and then contacted with a sufficient amount of acetone to form an acetone solution in which the fangchinoline is dissolved, further steps include contacting the acetone solution with a solid adsorbent which decolors and adsorbs a portion of the impurities, separating the adsorbent from the acetone solution, recovering fangchinoline crystals from the acetone solution, contacting the crystals from the acetone solution with a sufficient quantity of benzene to form a benzene solution in which the fangchinoline crystals are dissolved, recovering fangchinoline crystals at 4° C. from the benzene solution, contacting the fangchinoline crystals recovered from the benzene solution with a sufficient quantity of alcohol to form an alcohol solution in which the fangchinoline crystals are dissolved, and recovering purified fangchinoline crystals from the alcohol solution.

SPECIFIC DISCUSSION

The initial steps, involving extraction of tetrandrine and fangchinoline, along with cyclanoline and undesirable impurities, and separation of the cyclanoline from tetrandrine and fangchinoline, are similar to the initial steps of the second known method disclosed above. First, ground roots of Stephania Tetrandra are macerated with an acid solution, such as a 1% sulfuric acid solution, to leach tetrandrine and fangchinoline from the roots. Cyclanoline and other undesirable impurities are also leached from those roots during this step. The acid solution containing tetrandrine and other compounds leached from the roots are separated from the depleted roots, such as by sedimentation and decantation or filtration. The depleted roots separated from the acid solution are preferably macerated with fresh acid solution to extract additional tetrandrine and fangchinoline from the roots. Most preferably, raw material comprising ground roots of Stephania Tetrandra are macerated with fresh acid solution 4 times. The amount of tetrandrine and fangchinoline which can be recovered by macerating the same roots with fresh acid solution more than 4 times is generally insufficient to justify repeating the step more than 4 times.

The filtered acid solution, containing dissolved tetrandrine, fangchinoline, cyclanoline and other impurities is basified to cause the tetrandrine and fangchinoline to precipitate. Various bases may be used for basifying the acidic solution. However, hydroxides of alkali and alkaline-earth metals are preferred, especially calcium hydroxide and sodium hydroxide. Saturated mixture of calcium hydroxide and water (lime cream) is particularly preferred because the precipitates which are formed tend to settle faster than when sodium hydroxide is used. Higher product yields are generally achieved when calcium hydroxide is used. Although almost all of the tetrandrine and fangchinoline extracted from the roots of Stephania Tetrandra are precipitated, the majority of the precipitate is comprised of impurities which must be removed. However, substantially all of the cyclanoline remains in solution after basification of the acid solution containing the compounds extracted from the roots of Stephania Tetrandra.

Approximately 65 kilograms of precipitate can be obtained from 1 metric ton of roots of Stephania Tetrandra. The precipitate is separated from the basified solution, such as by sedimentation and decantation or filtration. The precipitate which is recovered from the basified solution is dried (e.g., at about 60° C.) and ground into granules. The dried granules are then contacted with chloroform. Tetrandrine and fangchinoline are soluble in chloroform. However, a very substantial portion of the undesirable impurities are not soluble in chloroform. After substantially all of the tetrandrine and fangchinoline has dissolved into the chloroform, any remaining undissolved solid material is separated from the chloroform solution, such as by sedimentation and decantation or filtration. The chloroform filtrate contains substantially all of the tetrandrine and fangchinoline which was present in the precipitate before it was contacted with the chloroform, whereas the solid materials filtered from the chloroform solution do not contain a substantial amount of tetrandrine or fangchinoline.

After the chloroform solution has been filtered, chloroform is removed, such as by evaporation and retrieved. Upon removal of the chloroform, a resulting solid residue is obtained. This solid residue is dried (e.g., at 60° C.) and ground into granules. Approximately 17 kilograms of dry residue is recovered from the chloroform solution for 1 ton of raw material. Accordingly, approximately 48 kilograms of undesirable impurities are removed from every 65 kilograms of precipitate obtained from the basified solution by contacting the precipitate with chloroform and separating any undissolved impurities from the chloroform solution.

The dried granules obtained from the chloroform solution are macerated with cool benzene. At relatively low temperatures, such as temperatures below normal room temperature (e.g., below about 20° C.), tetrandrine is soluble in benzene, but fangchinoline is only slightly soluble in benzene at low temperatures. In general, the ratio of the solubility of tetrandrine in benzene relative to the solubility of fangchinoline in benzene increases as temperature decreases. A suitable procedure for macerating the solid materials (obtained from the chloroform extract) with benzene involves macerating the materials with benzene, allowing the macerated solids and benzene to set for at least approximately 4 hours at 4° C., and separating the benzene solution from any undissolved solid material, such as by filtration. The solid materials separated from the benzene solution may be, and preferably are, again macerated with additional cool benzene at approximately 4° C. This step may be similar to the previous step involving macerating with benzene, allowing the macerated solid material and benzene to set for approximately 4 hours at about 4° C., and then separating the solid materials from the benzene solution. This procedure is preferably performed as many as about 5 of 6 times on the solid materials obtained from the chloroform extract.

The filtered benzene solution contains most of the tetrandrine which was present in the chloroform extract, and very little, if any, of the fangchinoline which was present in the chloroform extract. Benzene is removed from the filtered benzene solution, such as by evaporation and retrieved. After the benzene has been removed, a resulting benzene extract is dissolved in acetone. A suitable quantity of acetone for dissolving the benzene extract is approximately 20 times the volume of the benzene extract. Substantially all of the benzene extract is dissolved in the acetone to form an acetone solution containing tetrandrine and some remaining impurities. Tetrandrine is then crystallized from the acetone solution. This may be accomplished by removing acetone from the solution, such as by evaporation and retrieved, and cooling the concentrated acetone solution. Desirably, a sufficient quantity of acetone is removed so that the final volume of the concentrated solution is approximately ¼ to ⅙ the volume of the original acetone solution. The crystallized tetrandrine is separated from the acetone solution, such as by filtration. A substantial portion of the impurities present in the benzene extract remain in the acetone solution. However, even at this stage, the crystallized tetrandrine is not regarded as being sufficiently pure for pharmacological use.

In order to further purify the tetrandrine, the crystals obtained from the acetone solution are again dissolved in benzene. A suitable volume of benzene for dissolving the tetrandrine crystallized from the acetone solution is approximately 5 to 6 times the volume of the crystallized tetrandrine. An adsorbent solid material (e.g., activated carbon) is added to the benzene solution in which the tetrandrine crystals have been dissolved. Any remaining fangchinoline is not dissolved. The remaining colored impurities tends to become adsorbed on the adsorbent material. The time required to adsorb the impurities from the benzene solution is at least approximately 30 minutes. The benzene solution is separated from the undissolved substances (fangchinoline and impurities which have been adsorbed on activated charcoal), such as by filtration. Benzene is then removed from the benzene solution separated from fangchinoline and the adsorbent material, such as by evaporation and retrieved.

The resulting residue is then dissolved in an alcohol solution. Alcohol solution, as used herein, refers to pure alcohol, ethyl alcohol —200 proof dehydrated alcohol. A suitable volume of alcohol for refluxing and dissolving the tetrandrine (recovered from the benzene solution which was separated from the fangchinoline and adsorbent) is approximately 20 times the volume of the residue. Tetrandrine is then recrystallized from the alcohol solution. This can be accomplished such as by cooling the alcohol solution. The recrystallized tetrandrine is separated from the alcohol solution, such as by filtration. A majority of any impurities remaining in the benzene solution (separated from the adsorbent material) remains in the alcohol solution. The crystalline material which is separated from the alcohol solution is substantially pure tetrandrine, suitable for pharmacological use. The process produces approximately 6 kilograms of purified tetrandrine for every metric ton of raw material (i.e., ground roots of Stephania Tetrandra).

The materials from the chloroform extract which remain undissolved upon maceration with benzene contain a substantial quantity of fangchinoline, and are therefore designated as crude fangchinoline. The crude fangchinoline is dissolved in acetone. This requires approximately 20 parts by volume of acetone for each part by volume of crude fangchinoline. To the acetone solution in which the crude fangchinoline is dissolved there is added a solid adsorbent material (e.g., activated carbon). The activated carbon tends to decolor the acetone solution, whereas most of the fangchinoline remains in the acetone solution. The acetone solution (containing fangchinoline) is separated from the adsorbent upon which impurities have been adsorbed, such as by filtration.

After the adsorbent has been removed, acetone is removed from the acetone solution, such as by evaporation and retrieved. Desirably, a quantity of acetone is removed to achieve a volume of approximately ¼ to ⅙ of the volume of the acetone solution separated from the adsorbent. The acetone solution is then cooled to cause crystallization of the fangchinoline. The fangchinoline crystals still include some impurities, including tetrandrine. Although fangchinoline is hard to dissolve in cool benzene (e.g., benzene at about 4° C.), fangchinoline is relatively soluble in warm benzene (e.g., benzene at above normal room temperature). Tetrandrine is more soluble than fangchinoline in benzene at low temperature. Accordingly, any residual tetrandrine can be separated from fangchinoline by dissolving the fangchinoline containing the residual impurities, including tetrandrine, in benzene and subsequently cooling the benzene to cause the fangchinoline to recrystallize. The recrystallized fangchinoline will not contain any significant amount of tetrandrine. Essentially all of the residual tetrandrine will remain in the cool benzene solution. Dissolution of the fangchinoline crystallized and separated from the acetone solution can be achieved by dissolving the crystals in a volume of benzene which is approximately 5 to 6 times the volume of the crystals, and by cooling the benzene solution to a temperature of about 4° C., where upon the fangchinoline will be insoluble. The purified fangchinoline crystals are then separated from the benzene solution, such as by filtration.

The fangchinoline is then dissolved in an alcohol solution. A suitable quantity of alcohol solution is approximately 20 times the volume of the fangchinoline. Alcohol solution, as used herein, refers to pure alcohol, ethyl alcohol —200 proof dehydrated alcohol. After the fangchinoline crystals have been dissolved and refluxed in the alcohol solution, alcohol is cooled to cause fangchinoline to recrystallize. After the fangchinoline is recrystallized and decolored from the alcohol solution, the crystals are separated from the solution, such as by filtration.

The resulting recrystallized fangchinoline is sufficiently pure for pharmacological use. Approximately 1 to 2 kilograms of fangchinoline can be obtained for every metric ton of raw material (i.e., ground roots of Stephania Tetrandra).

The method of the invention is suitable for small scale production, such as in a laboratory, or for large scale commercial production, as well as anything in between. The method does not require the use of chromatographic separation techniques, and is therefore quicker and less expensive than known techniques involving the use of chromatographic separation columns. The method of the invention also has the advantage of being able to achieve higher yields of tetrandrine while using lower amounts of hazardous benzene than another known method. The invention also has the advantage of providing fangchinoline in a pure form suitable for pharmacological use.

What is claimed is:

1. A method for obtaining purified tetrandrine from the roots of Stephania Tetrandra, comprising:
    a. obtaining, from roots of Stephania Tetrandra, an extract comprising tetrandrine, fangchinoline and compounds which constitute impurities;
    b. contacting the extract with chloroform to form a chloroform solution in which tetrandrine and fangchinoline are dissolved;
    c. separating the chloroform solution containing dissolved tetrandrine and fangchinoline from undissolved impurities;
    d. removing chloroform from the chloroform solution to obtain a chloroform extract solid having an enriched tetrandrine and fangchinoline content relative to the extract;
    e. contacting the chloroform extract solid with benzene, said benzene being free of chloroform or other solvent for fanghinoline, to form a combination comprising undissolved fangchinoline, and a benzene solution in which tetrandrine is dissolved;
    f. separating the benzene solution from the undissolved fangchinoline; and
    g. removing benzene from the benzene solution to form a benzene extract which comprises tetrandrine.

2. The method of claim 1 wherein step (c) is achieved by filtration.

3. The method of claim 1 wherein step (d) is achieved by evaporation of the chloroform.

4. The method of claim 1 wherein the benzene used in step (e) is at a temperature below 20° C.

5. The method of claim 1 wherein the benzene used in step (e) is at a temperature of about 4° C.

6. The method of claim 1 wherein step (f) is achieved by filtration.

7. The method of claim 1 further comprising a solids recycling step comprising contacting the chloroform extract solid from step (f) with additional benzene to form a benzene solution in order to recover additional tetrandrine from the chloroform extract solid, separating the benzene solution from the solid for further processing in accordance with steps (g) and (h).

8. The method of claim 7 wherein the solids recycling step is repeated a plurality of times.

9. The method of claim 1 which further comprises:
    h. subjecting the first benzene extract which comprises tetrandrine to further operations to obtain purified tetrandrine.

10. The method of claim 1 wherein step (g) is achieved by evaporation of the benzene.

11. A method for obtaining purified tetrandrine from the roots of Stephania Tetrandra, comprising:
    a. macerating the roots of Stephania Tetrandra in an acidic solution to leach tetrandrine from the roots;
    b. separating the acidic solution containing tetrandrine from the roots;
    c. adding a base to the acidic solution to form a basic solution and to cause precipitation of tetrandrine;
    d. separating the precipitate from the basic solution;
    e. contacting the precipitate with chloroform to form a combination comprising undissolved precipitate and a chloroform solution in which tetrandrine is dissolved;
    f. separating the chloroform solution containing dissolved tetrandrine from the undissolved precipitate;
    g. removing the chloroform from the chloroform solution to obtain a chloroform extract solid which comprises tetrandrine;
    h. macerating the chloroform extract solid which comprises tetrandrine in benzene, said benzene being free of chloroform or other solvent for fangchinoline, to form a combination comprising undissolved solids and a first benzene solution containing dissolved tetrandrine;
    i. separating the first benzene solution in which tetrandrine was dissolved form the undissolved solids; and
    j. removing benzene from the first benzene solution to form a first benzene extract which comprises tetrandrine.

12. The method of claim 11 wherein the acidic solution used to leach tetrandrine from the roots is a sulfuric acid solution.

13. The method of claim 11 wherein the acidic solution used to leach tetrandrine from the roots is approximately a 1% sulfuric acid solution.

14. The method of claim 11 wherein step (b) is achieved by sedimentation, decantation, filtration or a combination thereof.

15. The method of claim 11 further comprising the step of recycling the roots from step (b), macerating the roots again with an acidic solution to leach additional bisbenzylisoquinolines from the roots, and thereafter separating the acidic solution from the roots for further processing in accordance with steps (c) through (u).

16. The method of claim 11 wherein the recycling step is repeated with the roots recovered from the first recycling step.

17. The method of claim 11 wherein the base used in step (c) is a hydroxide of an alkali metal or an alkaline-earth metal.

18. The method of claim 11 wherein the base used in step (c) is lime cream of calcium hydroxide.

19. The method of claim 11 wherein step (d) is achieved by sedimentation, decantation, filtration or a combination thereof.

20. The method of claim 11 wherein step (f) is achieved by sedimentation, decantation, filtration or a combination thereof.

21. The method of claim 11 wherein step (g) is achieved by evaporation of the chloroform.

22. The method of claim 11 wherein the benzene used in step (h) is at a temperature below 20° C.

23. The method of claim 11 wherein the benzene used in step (h) is at a temperature of about 4° C.

24. The method of claim 11 wherein the step of macerating the chloroform extract solid in benzene is performed for at least 4 hours.

25. The method of claim 24 wherein the macerated solids and benzene from step (h) are allowed to set for at least 4 hours at 4° C. before performing step (i).

26. The method of claim 11 wherein step (i) is achieved by filtration.

27. The method of claim 11 further comprising a solid recycling step comprising macerating the undissolved solids from step (i) with additional benzene to form a benzene solution in order to recover additional tetrandrine from the solids, separating the benzene solution from the solids.

28. The method of claim 27 wherein the solids recycling step is repeated a plurality of times.

29. The method of claim 11 which further comprises:
   k. contacting the first benzene extract which comprises tetrandrine with acetone to form an acetone solution in which tetrandrine is dissolved;
   l. removing acetone from the acetone solution to obtain a concentrated acetone solution;
   m. cooling the concentrated acetone solution to cause formation of tetrandrine crystals;
   n. separating the tetrandrine crystals from the concentrated acetone solution;
   o. contacting the tetrandrine crystals with benzene to form a second benzene solution containing dissolved tetrandrine;
   p. contacting the second benzene solution containing dissolved tetrandrine with an adsorbent which adsorbs impurities, but which does not adsorb substantial quantities of tetrandrine;
   q. separating the second benzene solution containing dissolved tetrandrine from the adsorbent on which impurities have been adsorbed;
   r. removing benzene from the second benzene solution to obtain a second benzene extract which comprises tetrandrine;
   s. contacting the second benzene extract which comprises tetrandrine with alcohol to form an alcohol solution in which tetrandrine is dissolved;
   t. crystallizing pure tetrandrine from the alcohol solution; and
   u. separating the pure tetrandrine from the alcohol solution.

30. The method of claim 11 wherein step (j) is achieved by evaporation of the benzene.

31. The method of claim 29 wherein the volume of acetone used in step (k) is approximately 20 times the volume of the first benzene extract.

32. The method of claim 29 wherein step (l) is achieved by evaporating a portion of the acetone.

33. The method of claim 29 wherein a sufficient quantity of acetone is removed in step (l) so that the volume of the concentrated acetone solution is approximately ¼ to ⅙ the volume of the acetone solution formed in step (k).

34. The method of claim 29 wherein step (n) is achieved by filtration.

35. The method of claim 29 wherein the amount of benzene contacted with tetrandrine crystals in step (o) is approximately 5 to 6 times the volume of the tetrandrine crystals.

36. The method of claim 29 wherein the adsorbent used in step (p) is activated carbon.

37. The method of claim 29 wherein the second benzene solution and adsorbent of step (p) are contacted for at least 30 minutes.

38. The method of claim 29 wherein step (q) is achieved by filtration.

39. The method of claim 29 wherein step (r) is achieved by evaporating the benzene.

40. The method of claim 39 wherein the amount of alcohol solution used in step (s) is approximately 20 times the volume of the second benzene extract.

41. The method of claim 40 wherein the alcohol is pure alcohol.

42. The method of claim 41 wherein the alcohol is 200 proof dehydrated ethyl alcohol.

43. The method of claim 29 wherein step (t) is achieved by cooling the alcohol solution.

44. The method of claim 29 wherein step (u) is achieved by filtration.

45. A method for obtaining purified tetrandrine from the roots of Stephania Tetrandra, comprising:
   a. obtaining, from roots of Stephania Tetrandra, an extract comprising tetrandrine and compounds which constitute impurities;
   b. contacting the extract with chloroform to form a chloroform solution in which tetrandrine is dissolved;
   c. separating the chloroform solution containing dissolved tetrandrine from undissolved impurities;
   d. removing chloroform from the chloroform solution to obtain a first solid having an enriched tetrandrine content relative to the precipitate;
   e. contacting the first solid with benzene, said benzene being free of chloroform or other solvent for fangchinoline, to form a combination comprising undissolved impurities and a benzene solution in which tetrandrine is dissolved;
   f. separating the benzene solution from the undissolved impurities form the first solid;
   g. removing benzene from the first benzene solution to form a first benzene extract which comprises tetrandrine; and
   h. contacting said undissolved impurities from said first solid with acetone to extract fangchinoline therefrom.

46. The method of claim 45 which further comprises:
   i. contacting the acetone solution with a solid adsorbent which preferentially decolors and adsorbs a portion of the impurities;
   j. separating the adsorbent on which impurities are adsorbed from the acetone solution in which fangchinoline is dissolved;
   k. recovering fangchinoline from the acetone solution;
   l. contacting the fangchinoline recovered from the acetone solution with a sufficient quantity of benzene to form a benzene solution in which the fangchinoline is undissolved at 4° C.;
   m. recovering fangchinoline crystals from the benzene solution;
   n. contacting the fangchinoline crystals recovered from the benzene solution with a sufficient quantity of alcohol to form an alcohol solution in which the fangchinoline crystals are dissolved; and
   o. crystallizing and recovering purified fangchinoline from the alcohol solution.

* * * * *

UNITED STATES PATENT AND TRADEMARK OFFICE
CERTIFICATE OF CORRECTION

PATENT NO.    : 6,218,541 B1
DATED         : April 17, 2001
INVENTOR(S)   : Zhishuang (NMI) Wang It is certified that error appears in the above-identified patent and that said Letters Patent is hereby corrected as shown below:

Column 5,
Line 6, "retrieved" should be -- retrival --;

Column 7,
Line 19, "5 or 6" should be -- 5 to 6 --;
Line 53, "tends" should be -- tend --;

Column 10, claim 11,
Line 21, "form" should be -- from --;

Column 12, claim 45,
Line 34, "form" should be -- from --.

Signed and Sealed this

Eighth Day of January, 2002

Attest:

JAMES E. ROGAN
*Attesting Officer*    *Director of the United States Patent and Trademark Office*